United States Patent
Kado et al.

(10) Patent No.: US 11,147,647 B2
(45) Date of Patent: Oct. 19, 2021

(54) MEDICAL STEREOSCOPIC OBSERVATION DEVICE, MEDICAL STEREOSCOPIC OBSERVATION METHOD, AND PROGRAM

(71) Applicant: Sony Olympus Medical Solutions Inc., Tokyo (JP)

(72) Inventors: Masataka Kado, Kanagawa (JP); Tomonori Ishikawa, Tokyo (JP); Gakuji Higuchi, Tokyo (JP); Hiroshi Ushiroda, Tokyo (JP); Takahiro Yamamoto, Tokyo (JP); Masashige Kimura, Tokyo (JP)

(73) Assignee: SONY OLYMPUS MRDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/087,409

(22) PCT Filed: Jan. 24, 2017

(86) PCT No.: PCT/JP2017/002332
§ 371 (c)(1),
(2) Date: Feb. 28, 2019

(87) PCT Pub. No.: WO2017/169014
PCT Pub. Date: Oct. 5, 2017

(65) Prior Publication Data
US 2019/0192251 A1    Jun. 27, 2019

(30) Foreign Application Priority Data
Mar. 30, 2016  (JP) .............................. JP2016-069714

(51) Int. Cl.
*H04N 13/128*  (2018.01)
*H04N 13/00*  (2018.01)
(Continued)

(52) U.S. Cl.
CPC .............. *A61B 90/20* (2016.02); *A61B 3/132* (2013.01); *G02B 21/0012* (2013.01);
(Continued)

(58) Field of Classification Search
CPC ....... A61B 1/00193; A61B 90/30; A61B 1/05; A61B 1/00009; A61B 90/361;
(Continued)

(56) References Cited

U.S. PATENT DOCUMENTS 5,742,429 A   4/1998  Tsumanuma et al.
6,157,337 A   12/2000 Sato
(Continued)

FOREIGN PATENT DOCUMENTS

CN   101518438 A   9/2009
CN   101702076 A   5/2010
(Continued)

OTHER PUBLICATIONS

International Search Report dated May 9, 2017, in PCT/JP2017/002332 filed Jan. 24, 2017.
(Continued)

*Primary Examiner* — Helen Shibru
(74) *Attorney, Agent, or Firm* — Xsensus LLP

(57) ABSTRACT

To reduce more load related to the correction of deformation of an observation image that is caused by an error between a plurality of imaging sections.
A medical stereoscopic observation device includes: an acquisition section configured to acquire, from an imaging unit including a first imaging section configured to capture a left-eye image and a second imaging section configured to capture a right-eye image, correction data for correcting an error related to capturing of an image between the first imaging section and the second imaging section, the imaging unit being rotatably held by a support section; and a
(Continued)

correction section configured to correct a difference of parallax between the left-eye image and the right-eye image on a basis of the correction data, using a position corresponding to a rotation axis of the imaging unit as a reference position.

12 Claims, 10 Drawing Sheets

(51) Int. Cl.
    *A61B 90/20* (2016.01)
    *G02B 21/36* (2006.01)
    *G02B 21/22* (2006.01)
    *G02B 21/00* (2006.01)
    *H04N 13/239* (2018.01)
    *A61B 3/13* (2006.01)
    *A61B 90/25* (2016.01)
    *A61B 90/00* (2016.01)

(52) U.S. Cl.
    CPC .......... *G02B 21/22* (2013.01); *G02B 21/362* (2013.01); *H04N 13/128* (2018.05); *H04N 13/239* (2018.05); *A61B 90/25* (2016.02); *A61B 2090/367* (2016.02); *H04N 2013/0081* (2013.01)

(58) Field of Classification Search
CPC ... A61B 90/20; A61B 90/25; A61B 2090/367; G02B 21/361; G02B 21/362; G02B 21/22; G02B 21/0012; H04N 13/128; H04N 2013/0081; H04N 13/239; G06T 19/20
USPC .......................................................... 348/45
See application file for complete search history.

(56) References Cited

U.S. PATENT DOCUMENTS

| | | | |
|---|---|---|---|
| 2005/0046905 A1 | 3/2005 | Aizaki et al. | |
| 2008/0018735 A1 | 1/2008 | Aizaki et al. | |
| 2008/0253683 A1* | 10/2008 | Nakamura | G06K 9/03 382/276 |
| 2010/0188497 A1 | 7/2010 | Aizaki et al. | |
| 2011/0187834 A1* | 8/2011 | Morifuji | H04N 13/20 348/47 |
| 2011/0292227 A1* | 12/2011 | Nakazawa | H04N 13/207 348/218.1 |
| 2012/0113278 A1 | 5/2012 | Okada | |
| 2012/0154550 A1* | 6/2012 | Takagi | G06K 9/00 348/49 |
| 2013/0147918 A1* | 6/2013 | Kakuko | H04N 13/204 348/46 |
| 2014/0043437 A1* | 2/2014 | Ueda | H04N 13/296 348/46 |
| 2015/0002630 A1* | 1/2015 | Takachi | H04N 13/236 348/46 |
| 2015/0015684 A1* | 1/2015 | Youn | H04N 13/133 348/54 |
| 2016/0012643 A1* | 1/2016 | Kezele | G02B 27/0093 345/633 |
| 2016/0119608 A1* | 4/2016 | Shibazaki | H04N 5/225 348/49 |
| 2016/0345000 A1 | 11/2016 | Nishigaki et al. | |
| 2017/0026632 A1* | 1/2017 | Ishiga | H04N 13/257 |
| 2018/0125340 A1* | 5/2018 | Ishikawa | A61B 1/00193 |

FOREIGN PATENT DOCUMENTS

| | | |
|---|---|---|
| CN | 104954776 A | 9/2015 |
| EP | 1 333 305 A2 | 8/2003 |
| JP | H08-317424 A | 11/1996 |
| JP | 2003-511174 A | 3/2003 |
| JP | 2005-72967 A | 3/2005 |
| JP | 2008-28814 A | 2/2008 |
| JP | 2012-19399 A | 1/2012 |
| JP | 2012-103741 A | 5/2012 |
| JP | 2013-180185 A | 9/2013 |
| WO | 2015/198758 A1 | 12/2015 |
| WO | WO 2016/017482 A1 | 2/2016 |

OTHER PUBLICATIONS

Extended European Search Report dated Apr. 24, 2019 in corresponding European Application No. 17773564.4.

Office Action dated Aug. 21, 2020 in European Patent Application No. 201780018967.4, 19 pages.

* cited by examiner

MEDICAL STEREOSCOPIC OBSERVATION DEVICE, MEDICAL STEREOSCOPIC OBSERVATION METHOD, AND PROGRAM

TECHNICAL FIELD

The present disclosure relates to a medical stereoscopic observation device, a medical stereoscopic observation method, and a program.

BACKGROUND ART

Recently, due to advancements in surgical techniques and surgical equipment, surgeries for performing various treatments (also called microsurgery) while observing an affected site with an observation device for medical use, such as a surgical microscope or an endoscope, are coming to be conducted frequently. Also, such observation devices for medical use are not limited to devices that enable optical observation of the affected area, and also include devices that display an image of the affected area captured by an imaging section (camera) or the like as an electronic image on a display such as a monitor.

In addition, when displaying, on a display, an image of an affected area captured by an imaging section of an observation device, the image often is displayed as a flat two-dimensional (2D) image. However, since a sense of perspective is difficult to obtain from a 2D image, and the relative distance between the affected area and a treatment tool may be difficult to grasp, in recent years, technology that displays a captured image of an affected area as a stereoscopic three-dimensional (3D) image has also been developed.

In this manner, in an observation device (hereinafter, sometimes referred to as a "stereoscopic observation device") that displays a captured image of an affected area as a stereoscopic 3D image, for example, images of the affected area (hereinafter, also referred to as "viewpoint images") are captured by a plurality of imaging sections from mutually different viewpoints. Then, by causing left and right eyes to observe viewpoint images captured by mutually different imaging sections, it becomes possible to cause a user to observe an image of the affected area as a stereoscopic 3D image that is based on a parallax between the viewpoint images. For example, Patent Literature 1 discloses an example of a mechanism for causing, by capturing parallax images of a subject by a plurality of imaging sections, a stereoscopic 3D image of the subject to be observed on the basis of the parallax images.

CITATION LIST

Patent Literature

Patent Literature 1: U.S. Pat. No. 6,157,337A

DISCLOSURE OF INVENTION

Technical Problem

On the other hand, in the case of capturing viewpoint images by a plurality of imaging sections, due to an error related to the capturing of images between the plurality of imaging sections that is generated by the assembly or the like of a lens, a difference in sizes (magnification percentages) of an imaged subject (affected area), and a shift in center positions of images are generated between parallax images in some cases. By such a difference between the parallax images, deformation is generated in some cases in a stereoscopic 3D image (hereinafter, also referred to as an "observation image") of a subject to be observed on the basis of the parallax images.

Particularly in a stereoscopic observation device for medical use, there can be assumed a utilization form of observing an observation target affected area from different directions while rotating (e.g. while performing a pivot motion of) an imaging section around the affected area. In such a utilization form, in some cases, the deformation of an observation image that is caused by an error related to the capturing of images between a plurality of imaging sections (i.e. shift between parallax images to be captured) is likely to stand out in accordance with positions and attitudes of the imaging sections with respect to the affected area.

As a method of correcting the above-described deformation of the 3D image, for example, there is a method of detecting a shift between parallax images by performing image analysis processing on each of captured viewpoint images, and correcting the shift by image processing. Nevertheless, in this method, the detection of a shift between parallax images and the correction of the shift are performed in real time, and processing load of an image processing function increases, and power consumption eventually increases in some cases.

In view of the foregoing, the present disclosure proposes a medical stereoscopic observation device, a medical stereoscopic observation method, and a program that can reduce more load related to the correction of deformation of an observation image that is caused by an error between a plurality of imaging sections.

Solution to Problem

According to the present disclosure, there is provided a medical stereoscopic observation device including: an acquisition section configured to acquire, from an imaging unit including a first imaging section configured to capture a left-eye image and a second imaging section configured to capture a right-eye image, correction data for correcting an error related to capturing of an image between the first imaging section and the second imaging section, the imaging unit being rotatably held by a support section; and a correction section configured to correct a difference of parallax between the left-eye image and the right-eye image on a basis of the correction data, using a position corresponding to a rotation axis of the imaging unit as a reference position.

In addition, according to the present disclosure, there is provided a medical stereoscopic observation method including: acquiring, from an imaging unit including a first imaging section configured to capture a left-eye image and a second imaging section configured to capture a right-eye image, correction data for correcting an error related to capturing of an image between the first imaging section and the second imaging section, the imaging unit being rotatably held by a support section; and correcting, by a processor, a difference of parallax between the left-eye image and the right-eye image on a basis of the correction data, using a position corresponding to a rotation axis of the imaging unit as a reference position.

In addition, according to the present disclosure, there is provided a program for causing a computer to execute: acquiring, from an imaging unit including a first imaging section configured to capture a left-eye image and a second imaging section configured to capture a right-eye image, correction data for correcting an error related to capturing of an image between the first imaging section and the second imaging section, the imaging unit being rotatably held by a support section; and correcting a difference of parallax between the left-eye image and the right-eye image on a basis of the correction data, using a position corresponding to a rotation axis of the imaging unit as a reference position.

Advantageous Effects of Invention

As described above, according to the present disclosure, a medical stereoscopic observation device, a medical stereoscopic observation method, and a program that can reduce more load related to the correction of deformation of an observation image that is caused by an error between a plurality of imaging sections are provided.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
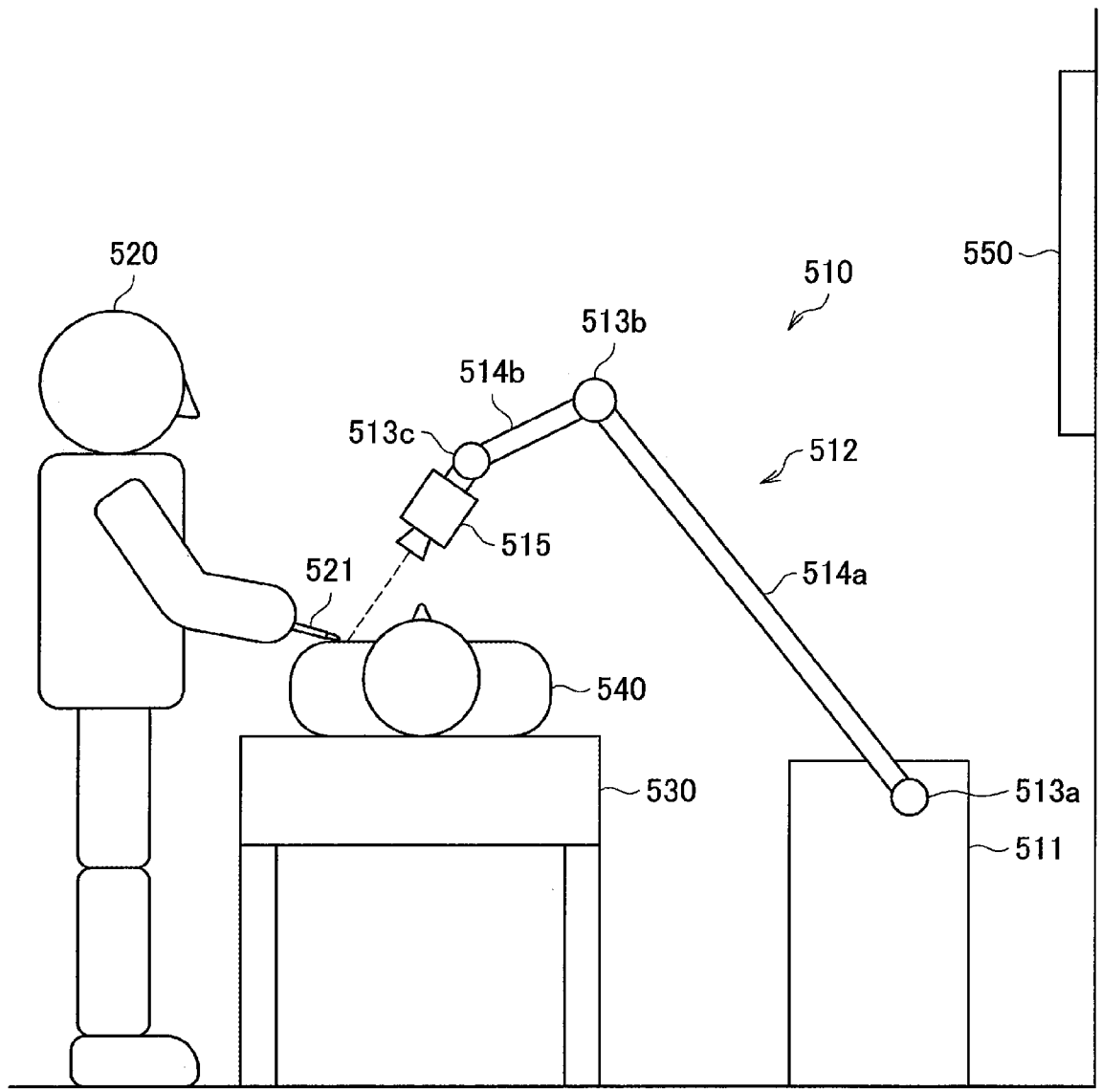
FIG. 1 is an explanatory diagram for explaining an applied example of a medical stereoscopic observation device according to an embodiment of the present disclosure.

Hereinafter, (a) preferred embodiments) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. Overview of medical stereoscopic observation device
 1.1. Applied example of medical stereoscopic observation device
 1.2. Exterior appearance of medical stereoscopic observation device
2. Investigation of medical stereoscopic observation device
3. Functional configuration
4. Processes
 4.1. Processing related to correction of parallax difference
 4.2. Processing related to correction of lens position
5. Hardware configuration
6. Conclusion <<1. Overview of Medical Stereoscopic Observation Device>>
<1.1. Applied Example of Medical Stereoscopic Observation Device>

First, to further elucidate the present disclosure, an applied example of a medical stereoscopic observation device according to an embodiment of the present disclosure will be described.

FIG. 1 is an explanatory diagram for explaining an applied example of a medical stereoscopic observation device according to an embodiment of the present disclosure. FIG. 1 illustrates an example of a case for an applied example of using a medical stereoscopic observation device according to an embodiment of the present disclosure, in which a surgical video microscope device equipped with an arm is used as the medical stereoscopic observation device.

FIG. 1 diagrammatically illustrates how a medical procedure is performed using a surgical video microscope device according to the present embodiment. Specifically, referring to FIG. 1, a state is illustrated in which a physician acting as the surgeon (user) 520 is using a surgical tool 521, such as a scalpel, tweezers, or forceps, for example, to perform surgery on a subject (patient) 540 lying on an operating table 530. Note that in the following description, medical procedure is used as a collective term to denote various types of medical treatments performed by a physician acting as the user 520 on a patient acting as the subject 540, such as a surgery or an examination. Also, although the example illustrated in FIG. 1 illustrates a situation of surgery as an example of a medical procedure, the medical procedure in which the surgical video microscope device 510 is used is not limited to surgery, and may be any of various other types of medical procedures such as an examination using an endoscope.

Beside the operating table 530, the surgical video microscope device 510 according to the present embodiment is provided. The surgical video microscope device 510 is equipped with a base section 511 which acts as a base, an arm section 512 which extends from the base section 511, and an imaging unit 515 connected as a front edge unit on the front edge of the arm section 512. The arm section 512 includes multiple joint sections 513a, 513b, and 513c, multiple links 514a and 514b joined by the joint sections 513a and 513b, and the imaging unit 515 provided on the front edge of the arm section 512. In the example illustrated in FIG. 1, for the sake of simplicity, the arm section 512 includes three joint sections 513a to 513c and two links 514a and 514b, but in actuality, the degrees of freedom in the positions and the attitudes of the arm section 512 and the imaging unit 515 may be considered to appropriately configure factors such as the numbers and shapes of the joint sections 513a to 513c and the links 514a and 514b, and the directions of the drive shafts of the joint sections 513a to 513c, so as to achieve the desired degrees of freedom.

The joint sections 513a to 513c have a function of rotatably joining the links 514a and 514b to each other, and by driving the rotation of the joint sections 513a to 513c, the driving of the arm section 512 is controlled. Herein, in the following description, the position of each structural member of the surgical video microscope device 510 means the position (coordinates) in a space prescribed for drive control, while the attitude of each structural member means the direction (angle) with respect to an arbitrary axis in the space prescribed for drive control. Also, in the following description, the driving (or the drive control) of the arm section 512 refers to the driving (or the drive control) of the joint sections 513a to 513c, as well as to the position and attitude of each structural member of the arm section 512 being changed (or such change being controlled) by conducting the driving (or the drive control) of the joint sections 513a to 513c.

On the front edge of the arm section 512, the imaging unit 515 is connected as a front edge unit. The imaging unit 515 is a unit that acquires an image of an imaging target, and is a device such as a camera capable of capturing a moving image or a still image, for example. As illustrated in FIG. 1, the attitudes and the positions of the arm section 512 and the imaging unit 515 are controlled by the surgical video microscope device 510 so that the imaging unit 515 provided on the front edge of the arm section 512 captures the operating site of the subject 540. Note that the configuration of the imaging unit 515 connected as the front edge unit on the front edge of the arm section 512 is not particularly limited, and the imaging unit 515 may be configured as an endoscope or a microscope, for example. Additionally, the imaging unit 515 may also be configured to be attachable to and removable from the arm section 512. According to such a configuration, an imaging unit 515 depending on the usage scenario may be connected appropriately to the front edge of the arm section 512 as the front edge unit, for example. Note that although the description herein focuses on a case in Which the imaging unit 515 is applied as the front edge unit, obviously the front edge unit connected to the front edge of the arm section 512 is not necessarily limited to the imaging unit 515.

Also, at a position facing the user 520, a display device 550 such as a monitor or a display is installed. An image of the operating site captured by the imaging unit 515 is displayed as an electronic image on the display screen of the display device 550. The user 520 performs various treatments while looking at an electronic image of the operating site displayed on the display screen of the display device 550.

In this way, in the medical field, the present embodiment proposes performing surgery while imaging the operating site with the surgical video microscope device 510.

Particularly, the surgical video microscope device 510 according to an embodiment of the present disclosure (that is, a medical stereoscopic observation device) is configured to be able to acquire image data for displaying the imaging target as a three-dimensional image (3D image).

As a specific example, the surgical video microscope device 510 is provided with a stereo camera including two imaging section subsystems (for example, camera units) as the imaging unit 515, and thereby acquires, via each imaging section, images from multiple different viewpoints (in other words, viewpoint images).

Each of the multiple viewpoint images acquired by the imaging unit 515 is subjected to various types of image processing by an image processing device built into or externally attached to the surgical video microscope device 510, and then displayed on the display device 550 as a left-eye image and a right-eye image, respectively. Note that in this description, the right-eye image denotes a so-called parallax image having a set parallax for observing a viewpoint corresponding to the user's right eye, to enable the user to observe a 3D image. Similarly, the left-eye image denotes a parallax image having a set parallax for observing a viewpoint corresponding to the user's left eye, to enable the user to observe a 3D image.

Note that a variety of techniques have been proposed as a mechanism for enabling the user 520 to observe, as a 3D image, the images displayed on the display device 550 as the left-eye image and the right-eye image. As a specific example, there is a technique in which special-purpose eyeglasses are used to cause the left and right eyes to observe mutually different images (in other words, a left-eye image and a right-eye image). Also, in recent years, glasses-free 3D picture technology which enables the observation of a three-dimensional image without the use of special-purpose eyeglasses has also been proposed.

In addition, the circumstances in which a medical observation device as described above is used also include cases in which various information should be checked, including images of an affected area. Under such circumstances, usage patterns such as displaying images respectively on multiple displays or displaying multiple images inside a display may also be anticipated. As a specific example, a case is anticipated in which an overall picture of the affected area is displayed on one display, while a magnified image of the affected area is displayed on another display. As another example, a case is also anticipated in which an image of the affected area is displayed on one display, while an image captured by another imaging device, such as a computed tomography (CT) image or a magnetic resonance imaging (MRI) image, is displayed on another display. For this reason, multiple display devices 550 may also be provided in some cases.

The above thus references FIG. 1 to describe, as an applied example of using a medical stereoscopic observation device according to an embodiment of the present disclosure, an example of a case in which a surgical video microscope device equipped with an arm is used as the medical stereoscopic observation device.

<1.2. Exterior Appearance of Medical Stereoscopic Observation Device>

Figure 2:
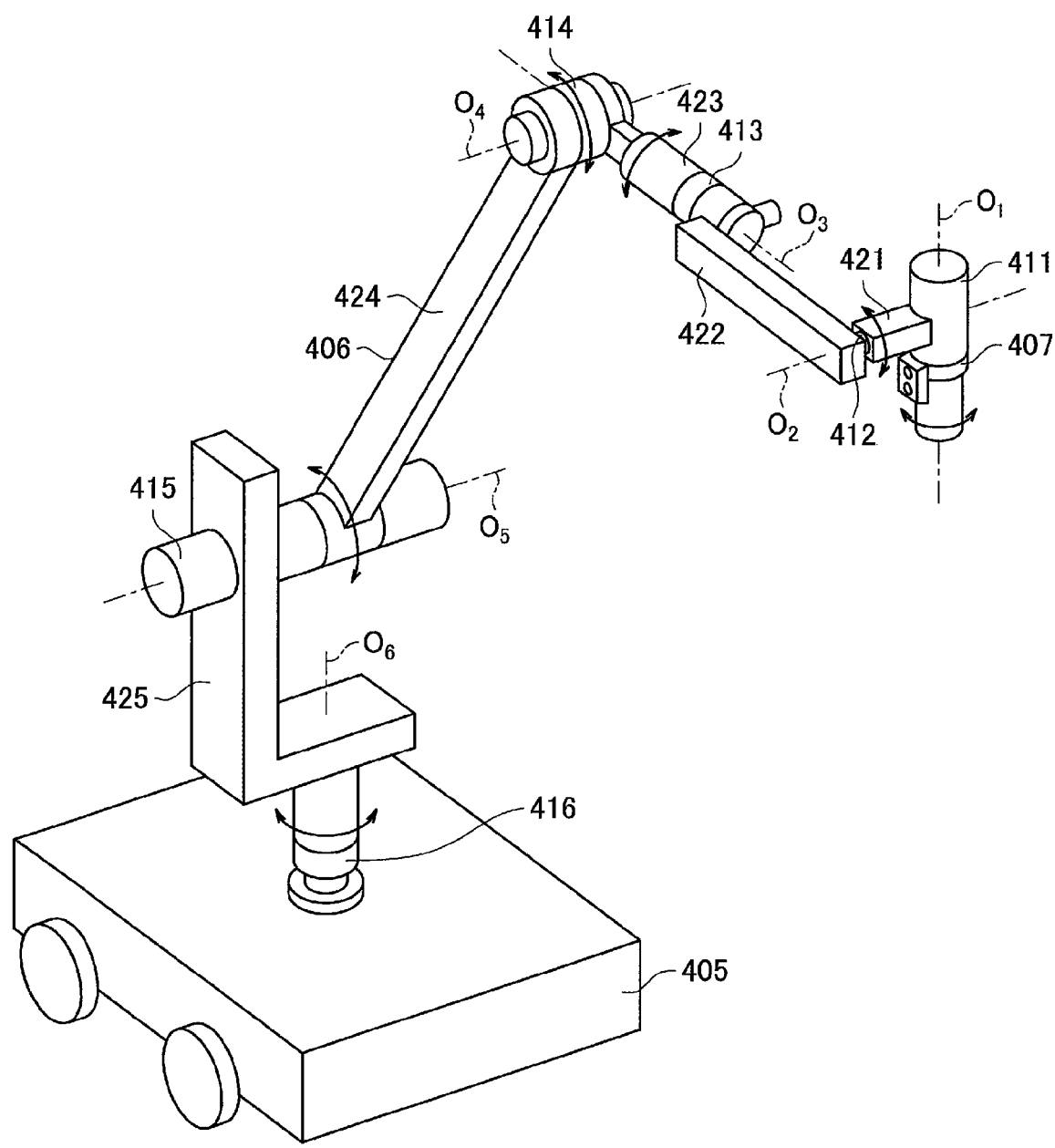
FIG. 2 is a schematic diagram illustrating an example of the exterior appearance of a medical stereoscopic observation device according to the embodiment.

Next, FIG. 2 will be referenced to describe a schematic configuration of a surgical video microscope device provided with an arm as an example of a surgical video microscope device (that is, a medical stereoscopic observation device) that acquires image data (that is, viewpoint images imaged from multiple viewpoints) for displaying an imaging target as a three-dimensional image, in a medical stereoscopic observation system according to an embodiment of the present disclosure. FIG. 2 is a schematic diagram illustrating an example of the exterior appearance of a medical stereoscopic observation device according to an embodiment of the present disclosure.

As illustrated in FIG. 2, an observation device 400 serving as an example of a medical stereoscopic observation device according to the present embodiment includes a base section 405, a support section 406, and an imaging unit 407. For example, the base section 405 is configured to be movable on a floor surface, and supports the support section 406. In addition, the imaging unit 407 is supported at the front edge of the support section 406.

The imaging unit 407 is a unit that acquires an image of an imaging target, and may be configured by a device such as a camera that captures a moving image or a still image, for example. The imaging unit 407 is configured as a microscope section, for example. Further, by controlling the driving of the support section 406, the position and attitude of the imaging unit 407 are controlled. In the present embodiment, the imaging unit 407 images a partial region of a patient's body, the partial region being an operating site, for example. Note that, as described above, in the observation device 400 according to the present embodiment, the imaging unit 407 is configured to be able to acquire images from multiple different viewpoints (that is, image data for displaying the imaging target as a three-dimensional image), like a stereo camera, for example.

For example, the support section 406 includes joint sections 411 to 416 and arm sections 421 to 425. For example, in the example illustrated in FIG. 2, four sets each including two arm sections, and a joint section that rotatably joints one (front edge side) of the two arm sections to the other one (rear edge side) are included.

The joint section 411 rotatably holds the imaging unit 407 on the front edge side, and is held by the arm section 421 on the rear edge side in a state of being fixed to the front edge section of the arm section 421. The joint section 411 has a cylindrical shape, and holds the imaging unit 407 so as to be rotatable around a first axis $O_1$ being a central axis in a height direction. The arm section 421 has a shape extending from the side surface of the joint section 411 in a direction orthogonal to the first axis $O_1$.

The joint section 412 rotatably holds the arm section 421 on the front edge side, and is held by the arm section 422 on the rear edge side in a state of being fixed to the front edge section of the arm section 422. The joint section 412 has a cylindrical shape, and holds the arm section 421 so as to be rotatable around a second axis $O_2$ being a central axis in the height direction, and an axis orthogonal to the first axis $O_1$. The arm section 422 has a substantially L-shape, and is joined to the joint section 412 at an edge section of a vertical line portion of the L-shape.

The joint section 413 rotatably holds a horizontal line portion of the L-shape of the arm section 422 on the front edge side, and is held by the arm section 423 on the rear edge side in a state of being fixed to the front edge section of the arm section 423. The joint section 413 has a cylindrical shape, and holds the arm section 422 so as to be rotatable around a third axis $O_3$ being a central axis in the height direction, an axis orthogonal to the second axis $O_2$, and an axis parallel to a direction in which the arm section 422 extends. The front edge side of the arm section 423 has a cylindrical shape, and a hole section penetrating through in a direction orthogonal to the height direction of the cylinder of the front edge side is formed on the rear edge side. The joint section 413 is rotatably held by the joint section 414 via the hole section.

The joint section 414 rotatably holds the arm section 423 on the front edge side, and is held by the arm section 424 on the rear edge side in a state of being fixed to the arm section 424. The joint section 414 has a cylindrical shape, and holds the arm section 423 so as to be rotatable around a fourth axis $O_4$ being a central axis in the height direction, and an axis orthogonal to the third axis $O_3$.

The joint section 415 rotatably holds the arm section 424 on the front edge side, and is fixedly attached to the arm section 425 on the rear edge side. The joint section 415 has a cylindrical shape, and holds the arm section 424 so as to be rotatable around a fifth axis $O_5$ being a central axis in the height direction, and an axis parallel to the fourth axis $O_4$. The arm section 425 includes a portion having an L-shape, and a rod-shaped portion extending downward from a horizontal line portion of the L-shape. The joint section 415 is attached to an edge section of a vertical line portion of the L-shape of the arm section 425 on the rear edge side.

The joint section 416 rotatably holds the arm section 425 on the front edge side, and is fixedly attached to the top surface of the base section 405 on the rear edge side. The joint section 416 has a cylindrical shape, and holds the arm section 425 so as to be rotatable around a sixth axis $O_6$ being a central axis in the height direction, and an axis orthogonal to the fifth axis $O_5$. A rear edge section of the rod-shaped portion of the arm section 425 is attached to the front edge side of the joint section 416.

The support section 406 having the configuration described above realizes motions with six degrees of freedom in total having three translational degrees of freedom and three rotational degrees of freedom in the imaging unit 407 (microscope section).

Figure 3:
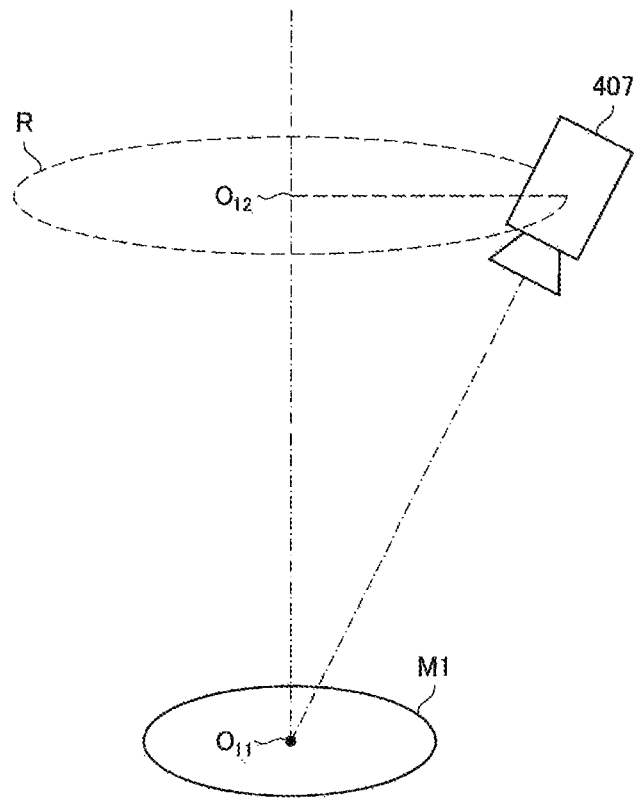
FIG. 3 is an explanatory diagram for explaining an example of a utilization form of an observation device according to the embodiment.

For example, FIG. 3 is an explanatory diagram for explaining an example of a utilization form of an observation device according to the present embodiment. In the example illustrated in FIG. 3, a focal point of the imaging unit 407 is fixed to a position $O_{11}$ on an affected area M1, and an image of the affected area M1 is being captured while moving (i.e. while performing a pivot motion of) the imaging unit 407 along a circular orbit R centering on a position denoted by a reference numeral $O_{12}$. By such control, it becomes possible to observe a desired position of the affected area M1 from versatile directions by rotating the imaging unit 407 about the desired position (i.e. the focal position $O_{11}$) of the affected area M1. Note that in the following description, an observation method (utilization form) as illustrated in FIG. 3 will also be referred to as "pivot observation".

<<2. Investigation of Medical Stereoscopic Observation Device>>

Figure 4:
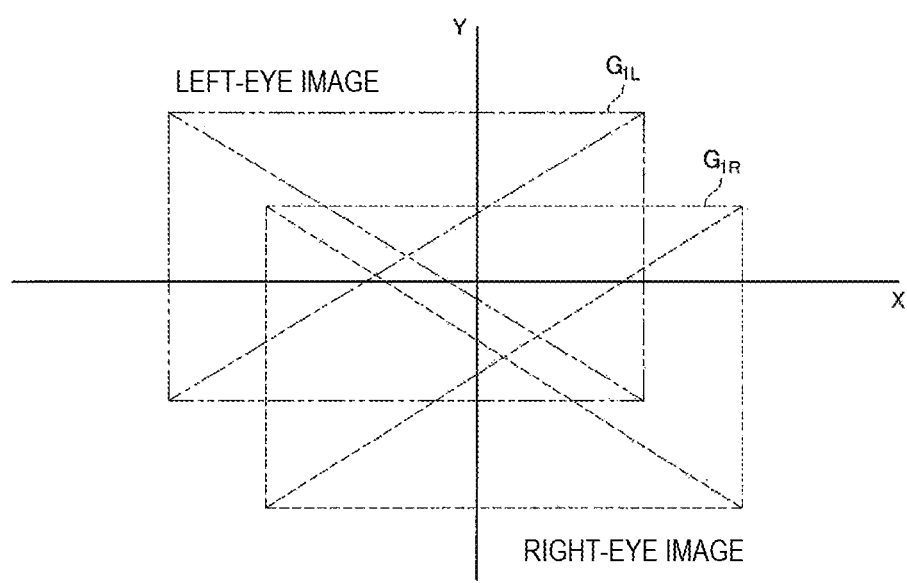
FIG. 4 is a diagram diagrammatically illustrating a situation in which a parallax difference is generated.

Next, for making features of the medical stereoscopic observation device according to the present embodiment more understandable, a problem of the medical stereoscopic observation device will be organized with reference to FIG. 4. FIG. 4 is an explanatory diagram for explaining a problem of the medical stereoscopic observation device according to the present embodiment.

In a stereoscopic observation device that causes an image of an observation target (affected area) to be observed as a stereoscopic 3D image, as described above, for example, images (i.e. viewpoint images) of the observation target are acquired from a plurality of different viewpoints by an imaging unit (so-called stereo camera) including a plurality of imaging sections. Then, the viewpoint images captured by the respective imaging sections are controlled so as to be observed by mutually different eyes of a right eye and a left eye of the user. According to such a configuration, it becomes possible for the user to observe an image of the observation target as a stereoscopic 3D image.

On the other hand, due to the variations or the like in the assembly of an optical system such as a lens that are generated between the plurality of imaging sections constituting the imaging unit, a shift in center positions of images (hereinafter, also referred to as a "parallax difference") or a difference in sizes (hereinafter, also referred to as a "magnification difference") of an imaged subject (an affected area) is generated in some cases between viewpoint images captured by the respective imaging sections.

For example, FIG. 4 is a diagram diagrammatically illustrating a situation in which a parallax difference is generated. In FIG. 4, a reference numeral $G_{1L}$ diagrammatically illustrates a range in which a parallax image (left-eye image) for causing a left eye to observe is to be captured. In addition, a reference numeral $G_{1R}$ diagrammatically illustrates a range in which a parallax image (right-eye image) for causing a right eye to observe is to be captured. As illustrated in FIG. 4, under a situation in which a parallax difference is generated, when the user is caused to observe the parallax images as-is, the user observes the images with the shifted imaging ranges by the left and right eyes, and the parallax difference stands out as deformation of a 3D image in some cases.

More specifically, it is desirable to assemble an optical system or the like of each of the imaging sections such that the respective centers of parallax images (e.g. a left-eye image and a right-eye image) to be captured by a plurality of imaging sections, and a central axis in the height direction that is provided for rotating the imaging unit (i.e. the first axis $O_1$ illustrated in FIG. 2) substantially match on an XY plane illustrated in FIG. 4. Nevertheless, as described above, due to the variations or the like in the assembly of an optical system such as a lens, a shift is generated in some cases between the center of a parallax image to be captured by at least any of a plurality of imaging sections, and a position that is based on the above central axis. By such a shift, the above-described parallax difference stands out in some cases.

In addition, under a situation in which a magnification difference is generated, in parallax images respectively captured by a plurality of imaging sections, an observation target is imaged at mutually different magnification percentages. Thus, under a situation in which a magnification difference is generated, when the user is caused to observe parallax images as-is, the user observes the images with mutually different magnification percentages by the left and right eyes, and the magnification difference stands out as deformation of a 3D image in some cases, similarly to a case in which a parallax difference is generated.

As a method of correcting such deformation of a 3D image that is caused by the parallax difference, the magnification difference, or the like, for example, there is a method of detecting a shift between viewpoint images by performing image analysis processing on each of captured viewpoint images, and correcting the shift by image processing. Nevertheless, in this method, the detection of a shift between viewpoint images and the correction of the shift are performed in real time, and processing load of an image processing function increases, and power consumption eventually increases in some cases.

In view of the foregoing, the present disclosure proposes a mechanism that can reduce more processing load related to the correction of deformation of a 3D image (i.e. an observation image) that is generated by a shift between viewpoint images that is caused by an error between a plurality of imaging sections, such as a parallax difference and a magnification difference. Thus, in the following description, the medical stereoscopic observation device according to the present embodiment will be described in more detail.

<<3. Functional Configuration>>

Figure 5:
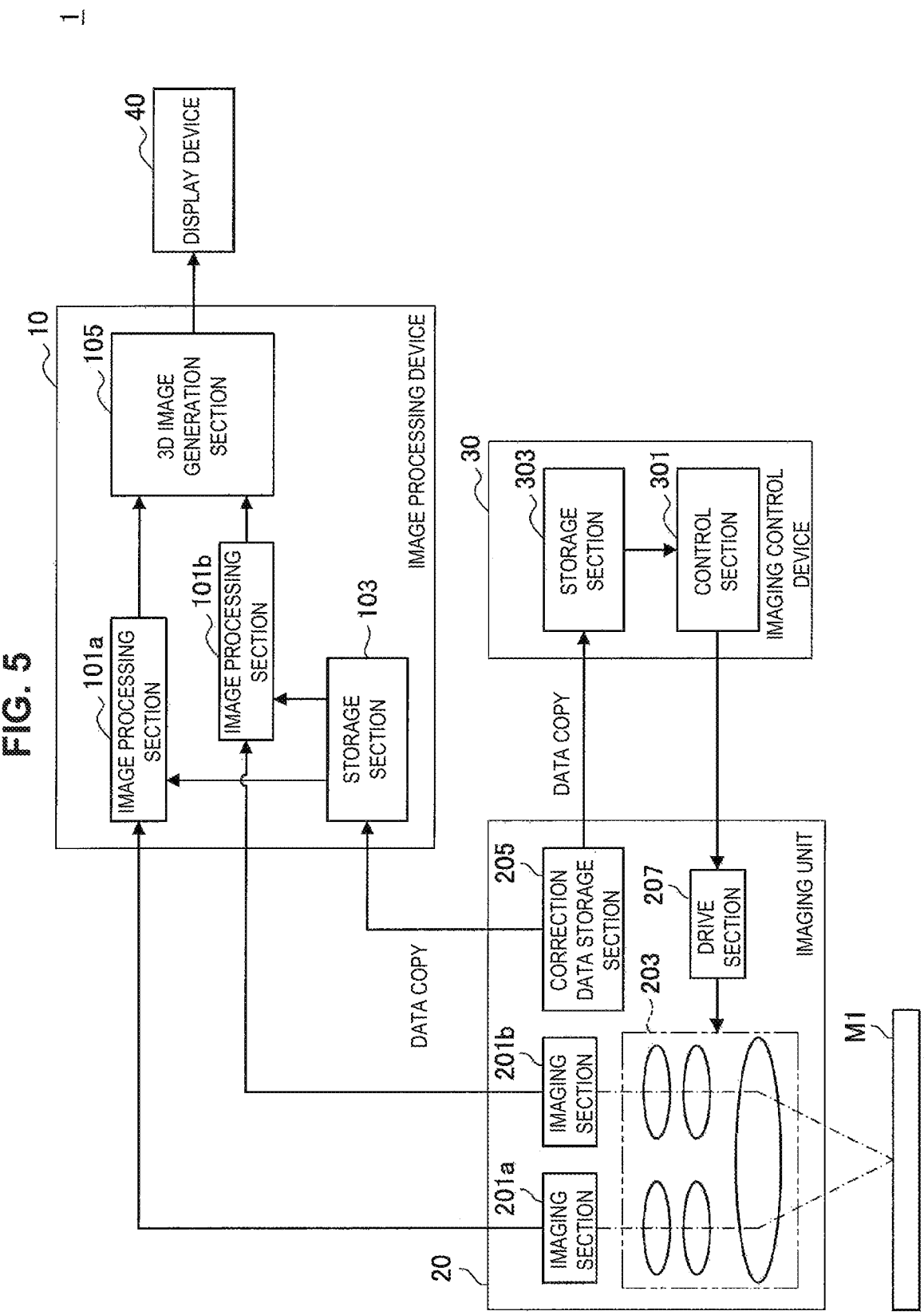
FIG. 5 is a block diagram illustrating an example of a functional configuration of a medical stereoscopic observation device according to the embodiment.

First of all, an example of a functional configuration of the medical stereoscopic observation device according to the present embodiment will be described with reference to FIG. 5. FIG. 5 is a block diagram illustrating an example of a functional configuration of the medical stereoscopic observation device according to the present embodiment.

As illustrated in FIG. 5, a medical stereoscopic observation device 1 according to the present embodiment includes an imaging unit 20, an image processing device 10, an imaging control device 30, and a display device 40.

The imaging unit 20 corresponds to the imaging unit 515 described with reference to FIG. 1, and may be configured as a microscope, for example. Specifically, as illustrated in FIG. 5, the imaging unit 20 includes imaging sections 201a and 201b, an optical system 203, a correction data storage section 205, and a drive section 207, for example.

The imaging sections 201a and 201b may include an image sensor such as a complementary metal-oxide semiconductor (CMOS) image sensor or a charge-coupled device (CCD) image sensor, for example. Note that in the following description, the imaging sections 201a and 201b may be designated simply the "imaging section 201" when not being particularly distinguished.

The imaging sections 201a and 201b capture images of an imaging target from mutually different viewpoints, and output the respective captured viewpoint images to the image processing device 10 to be described later. The imaging sections 201a and 201b may be configured to be able to capture a moving image. Note that, for the sake of convenience, this description will be given assuming that the imaging section 201a captures a left-eye image, and the imaging section 201b captures a right-eye image.

The optical system 203 includes various lenses such as a focus lens and a zoom lens, and is a configuration for forming an image of an imaging target on an image sensor of the imaging section 201. The lenses included in the optical system 203 may be configured to be movable on an optical axis. For example, by a position of the focus lens on the optical axis being controlled, a position of a focal point of the optical system 203 is controlled. In addition, by a position of the zoom lens on the optical axis being controlled, a magnification percentage of zoom of the optical system 203 (i.e. zoom position) is controlled.

The drive section 207 includes, for example, a motor, a driver circuit that supplies drive current to the motor, and the like, and moves the lenses (e.g. the focus lens and the zoom lens) included in the optical system 203, along the optical axis. Note that an operation of the drive section 207 is controlled by the imaging control device 30 to be described later.

The correction data storage section 205 is a storage region, that stores correction data for correcting various differences caused by an error between the imaging sections 201a and 201b. The correction data storage section 205 is configured by a nonvolatile memory such as an Electrically Erasable Programmable Read-Only Memory (EEPROM), for example. In addition, the correction data includes data for connecting a difference between viewpoint images respectively captured by the imaging sections 201a and 201b, such as the above-described parallax difference and magnification difference, for example. In addition, the correction data may include data for correcting a difference (variation) in properties between respective imagers of the imaging sections 201a and 201b.

Figure 6:
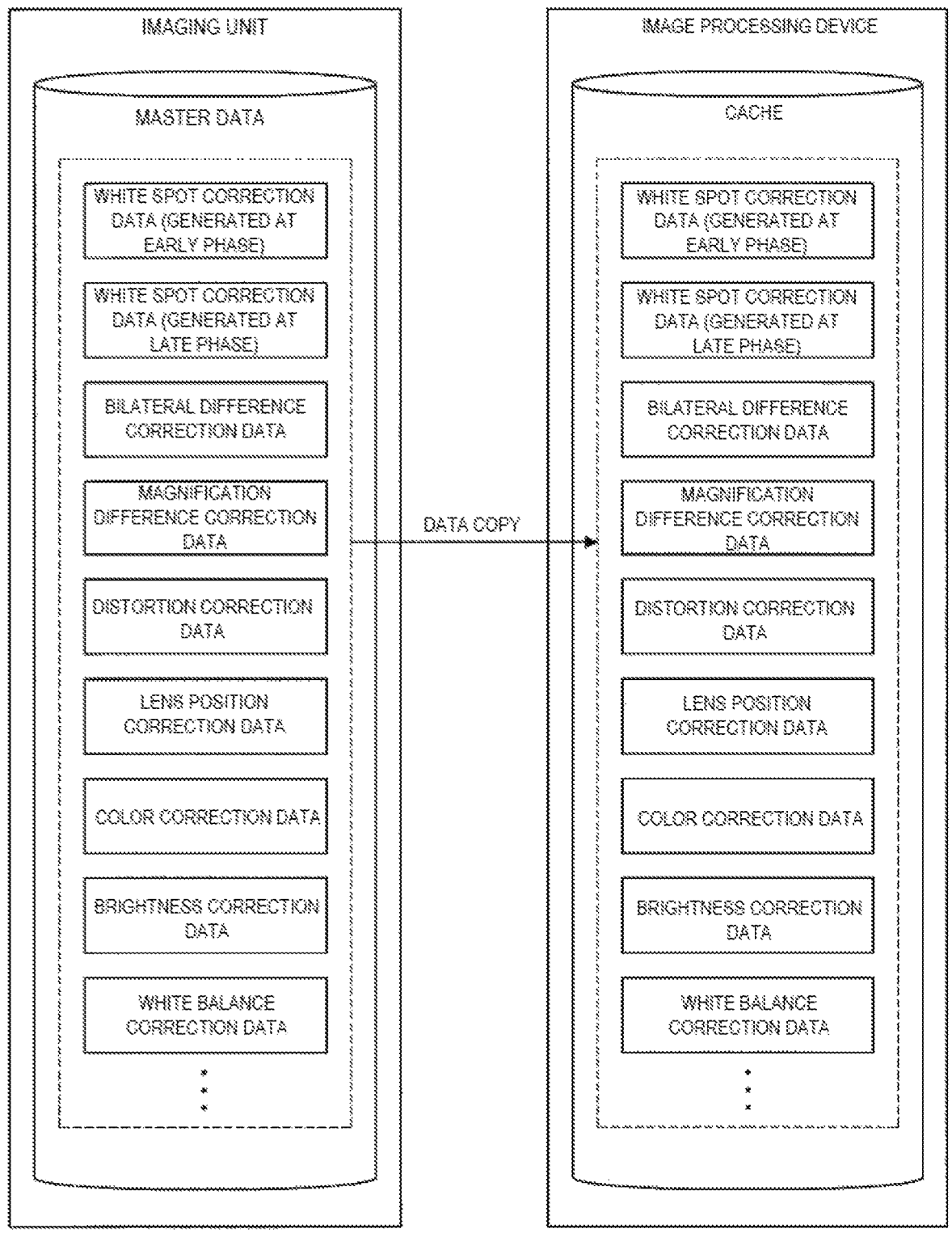
FIG. 6 is an explanatory diagram for explaining an example of correction data in this embodiment.

For example, FIG. 6 is an explanatory diagram for explaining an example of correction data in the present embodiment. In FIG. 6, data shown as master data indicates an example of correction data to be stored in the correction data storage section 205 of the imaging unit 20. Specifically, the correction data (master data) includes various data such as data for adjusting a bilateral difference of a lens optical system, such as a parallax difference, a magnification difference, and distortion, for example, data for adjusting an individual variation of a lens optical system, such as a lens position, and data for adjusting an individual variation between imagers, such as color, brightness, white balance, and a white spot.

White spot correction data is data for correcting a defect of partial dots in an image (so-called white spot) that is generated by pixel defects of an imager. The pixel defects of an imager include an initial defect existing at the time of shipment of the imaging unit 20, and a defect generated at a later phase, such as an aging degradation and a failure. Thus, data for correcting a white spot generated from an early phase, and data for correcting a white spot generated at a late phase may be stored as white spot correction data.

Bilateral difference correction data is data for correcting the above-described parallax difference. Specifically, for example, the bilateral difference correction data is generated on the basis of directions of shifts of centers of images (i.e. a left-eye image and a right-eye image) respectively captured by the imaging sections 201a and 201b, with respect to a predetermined reference position (e.g. a center between the imaging section 201a and the imaging section 201b), and amounts of the shifts. Examples of the reference position include a position (e.g. the position of the first axis $O_1$ on the XY plane) that is based on the central axis in the height direction that is provided for rotating an imaging unit (i.e. the first axis $O_1$ illustrated in FIG. 2), for example. In addition, for example, the reference position may be a position that is based on the center between the imaging section 201a and the imaging section 201b. For example, in the example illustrated in FIG. 4, an intersection point (i.e. origin) of an X-axis and a Y-axis corresponds to a reference position, and amounts of shifts in an X direction and a Y direction of the respective centers of the left-eye image and the right-eye image with respect to the reference position correspond to an example of information used as the bilateral difference correction data.

Figure 7:
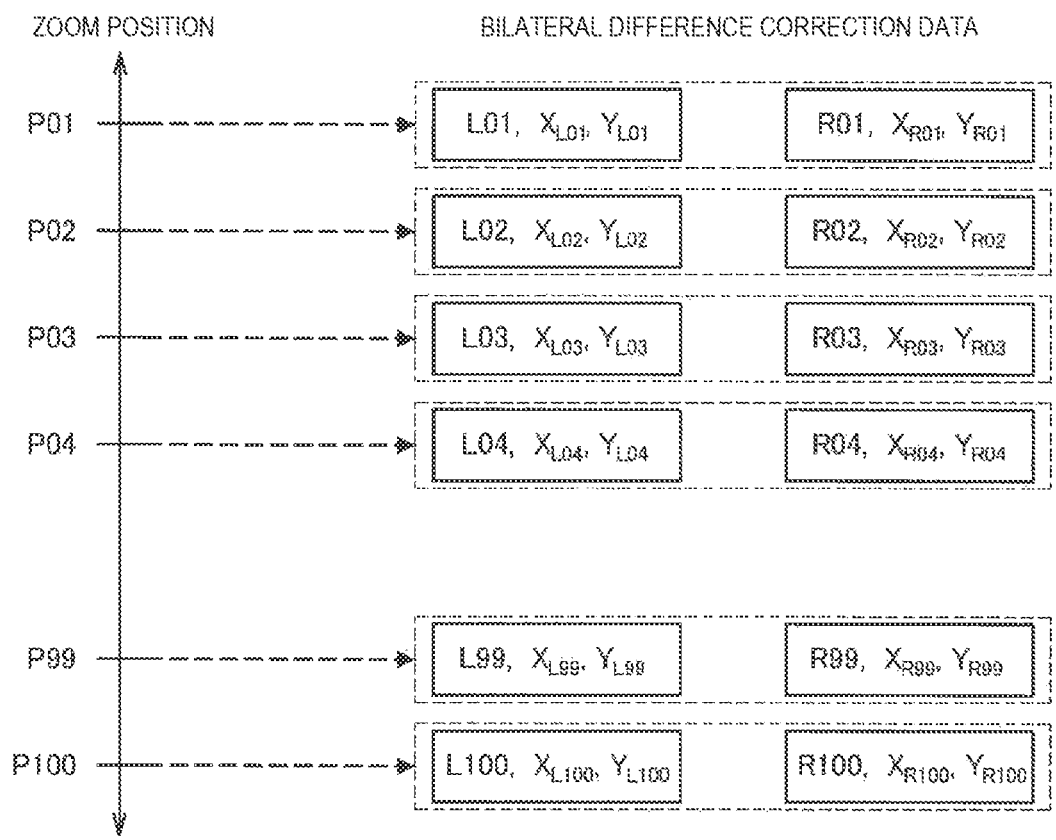
FIG. 7 is an explanatory diagram for explaining an example of bilateral difference correction data.

Note that, the shifts of the respective centers of the left-eye image and the right-eye image also vary depending on a zoom position (magnification percentage of zoom). Thus, the bilateral difference correction data may be stored for each zoom position. For example, FIG. 7 is an explanatory diagram for explaining an example of the bilateral difference correction data. In FIG. 7, reference numerals P01 to P100 respectively denote zoom positions. In addition, reference numerals L01 to L100 denote zoom positions on an imaging section side on which a left-eye image is to be captured, and respectively correspond to the zoom positions P01 to P100. In a similar manner, reference numerals R01 to R100 denote zoom positions on an imaging section side on which a right-eye image is to be captured.

In other words, in the example illustrated in FIG. 7, data that is based on a shift of a center position of a left-eye image, and data that is based on a shift of a center position of a right-eye image are stored as the bilateral difference correction data for each of the zoom positions P01 to P100.

For example, attention will be focused on bilateral difference correction data corresponding to the zoom position P01. In this case, for example, information L01 indicating a zoom position of the imaging section 201a, and information pieces $X_{L01}$ and $Y_{L01}$ indicating a shift of a center position of an image captured at the zoom position L01 are included as data for correcting a left-eye image captured by the imaging section 201a. Note that, data $X_{L01}$ indicates a shift in the X direction of the center position, and data $Y_{L01}$ indicates a shift in the Y direction of the center position. In a similar manner, information R01 indicating a zoom position of the imaging section 201b, and information pieces $X_{R01}$ and $Y_{R01}$ indicating a shift of a center position of an image captured at the zoom position R01 are included as data, for correcting a right-eye image captured by the imaging section 201b. Note that, data $X_{R01}$ indicates a shift in the X direction of the center position, and data $Y_{R01}$ indicates a shift in the Y direction of the center position. In addition, the same applies to the zoom positions P02 to P100.

In addition, among the master data (correction data) illustrated in FIG. 6, color correction data is data for correcting a difference in color properties between respective imagers of the imaging sections 201a and 201b. In addition, magnification difference correction data is data for correcting a difference in magnification percentages of zoom between the imaging sections 201a and 201b, that is to say, data for correcting the above-described magnification difference. In addition, lens position correction data is data for correcting a shift in lens positions that corresponds to a variation in assembly (i.e. individual variation) of each lens for forming an image of an imaging target on each of the imaging sections 201a and 201b. In addition, white balance correction data is data for correcting a difference in white balance between the respective imagers of the imaging sections 201a and 201b.

In addition, distortion correction data is data for correcting a variation in properties (deformation) of optical systems such as a lens. For example, when there is a variation in properties (e.g. distortion) of optical systems between the imaging sections 201a and 201b, the variation in properties stands out in some cases as deformation of a 3D image.

In addition, brightness correction data is data for correcting a difference in brightness (i.e. sensitivity) between the respective imagers of the imaging sections 201a and 201b. For example, in some cases, a difference in sensitivity between the respective imagers of the imaging sections 201a and 201b stands out as a difference in brightness between a left-eye image and a right-eye image, and causes asthenopia of the user viewing a 3D image.

Note that the above-described correction data are only required to be generated in accordance with the respective properties of the imaging sections 201a and 201b on the basis of a preliminary examination, experiment, or the like, for example, and prestored in the correction data storage section 205. For example, the bilateral difference correction data can be acquired by capturing images respectively by the imaging sections 201a and 201b at each zoom position. In addition, in a similar manner, the white spot correction data, the magnification difference correction data, the distortion correction data, the lens position correction data, the color correction data, the brightness correction data, and the white balance correction data can also be generated in advance on the basis of a result of a preliminary experiment, examination, or the like. In addition, in the correction data, partial data may be added or updated for correcting a difference generated by a factor generated at a late stage, as in the white spot correction data (generated at a late stage).

In addition, as illustrated in FIG. 6, at least part of the correction data stored in the imaging unit 20 as master data is transferred to the image processing device 10 and the imaging control device 30 at a predetermined timing (predetermined trigger) such as at the time of power input, and at the time when the imaging unit 20 is recognized, for example. Upon receiving the transfer of the data from the imaging unit 20, the image processing device 10 and the imaging control device 30 hold the data in respective storage regions (storage sections 103 and 303 to be described later) as cache. Note that an example of more specific processing performed by each of the image processing device 10 and the imaging control device 30 using the correction data will be separately described later.

The imaging control device 30 is a configuration for controlling an operation related to capturing of an image that is performed by the imaging unit 20. The imaging control device 30 is provided near a portion of the arm section 512 described with reference to FIG. 1, to which the imaging unit 20 is connected, for example. In addition, as illustrated in FIG. 5, the imaging control device 30 includes a control section 301 and the storage section 303.

The storage section 303 is a storage region for temporarily or permanently storing data for the imaging control device 30 implementing various functions. The storage section 303 is configured by a nonvolatile memory such as a flash memory and a Read-Only Memory (ROM), for example. In addition, the storage section 303 may include a main storage device including a volatile memory such as a Random Access Memory (RAM). In addition, at least partial data (hereinafter, the data will also be collectively referred to as "correction data") of the correction data stored in the correction data storage section 205 is transferred from the imaging unit 20 to the imaging control device 30. The correction data transferred from the imaging unit 20 is temporarily or permanently held in the storage section 303. Note that, at this time, the storage section 303 may hold, as cache, at least partial data of the correction data in a storage device having high access speed such as a RAM. In addition, the storage section 303 may hold, as cache, the correction data itself that has been transferred from the imaging unit 20.

The control section 301 is configured by a processor (an arithmetic processing apparatus) such as a Central Processing Unit (CPU), for example. The control section 301 controls an operation of the imaging unit 20 on the basis of data stored in the storage section 303. As a specific example, the control section 301 may control a lens position of each lens (e.g. the focus lens or the zoom lens) of the optical system 203 by controlling an operation of the drive section 207 of the imaging unit 20.

In addition, the control section 301 may correct various parameters related to capturing of images that is performed by the imaging unit 20, on the basis of correction data held in the storage section 303 as cache. For example, the control section 301 may correct a shift in lens positions (e.g. default positions of lenses) between lenses for forming images of an imaging target on the respective imaging sections 201a and 201b, on the basis of the lens position correction data described with reference to FIG. 6.

The image processing device 10 is a configuration for performing various types of image processing on an image captured by the imaging unit 20. For example, the image processing device 10 may be built into the base section 511 of the surgical video microscope device 510 described with reference to FIG. 1, or may be externally attached to the surgical video microscope device 510. In addition, as illustrated in FIG. 5, the image processing device 10 includes image processing sections 101a and 101b, the storage section 103, and a 3D image generation section 105.

The storage section 103 is a storage region for temporarily or permanently storing data for the image processing device 10 implementing various functions. The storage section 103 is configured by an auxiliary storage device including a nonvolatile memory such as a Solid State Drive (SSD), for example, or a main storage device including a volatile memory such as a Random Access Memory (RAM). In addition, at least partial data (hereinafter, the data will also be collectively referred to as "correction data") of the correction data stored in the correction data storage section 205 is transferred from the imaging unit 20 to an information processing device 10. The correction data transferred from the imaging unit 20 is temporarily or permanently held in the storage section 103. Note that, at this time, the storage section 103 may hold, as cache, at least partial data of the correction data in a storage device having high access speed such as a RAM. In addition, the storage section 103 may hold, as cache, the correction data itself that has been transferred from the imaging unit 20.

The image processing sections 101a and 101b are configurations for performing various types of image processing on respective viewpoint images captured by the imaging unit 20. For example, in the example illustrated in FIG. 5, the image processing section 101a acquires a viewpoint image (i.e. left-eye image) captured by the imaging section 201a, from the imaging section 201a, and performs various types of image processing on the acquired viewpoint image. In addition, the image processing section 101b acquires a viewpoint image (i.e. right-eye image) captured by the imaging section 201b, from the imaging section 201b, and performs various types of image processing on the acquired viewpoint image. Note that the image processing sections 101a and 101b have configurations similar to each other except that viewpoint images to be processed are different. Thus, in this description, a more detailed operation will be described with focusing attention on the image processing section 101a, and more detailed description of the image processing section 101b will be omitted.

For example, by performing image analysis on the acquired viewpoint image, the image processing section 101a may extract a target (e.g. a specific site or focus of disease) satisfying a predetermined condition, and perform so-called enhancement processing on the extracted target. In addition, as another example, the image processing section 101a may superimpose (fuse) an image captured by another imaging device such as a Computed Tomography (CT) and a Magnetic Resonance Imaging (MRI), onto the acquired viewpoint image. It should be appreciated that the image processing section 101a may operate so as to perform minimum image processing for causing the acquired viewpoint image to be displayed as an electronic image.

In addition, the image processing section 101a may correct a difference between another viewpoint image (right-eye image) that is generated by an error between the imaging section 201a and the imaging section 201b, with respect to the acquired viewpoint image (left-eye image), on the basis of correction data held in the storage section 103 (or cache of the correction data). For example, the image processing section 101a may correct a parallax difference between the left-eye image and the right-eye image on the basis of the bilateral difference correction data described with reference to FIG. 6. Note that, at this time, the image processing section 101a may correct a parallax difference between viewpoint images (i.e. between the left-eye image and the right-eye image) using, as a reference position, the focal position $O_{11}$ of the imaging unit 20 (i.e. a position serving, as a reference of the rotation of the imaging unit 20) at the time of pivot observation as illustrated in FIG. 3, for example. Note that the focal position $O_{11}$ can be recognized on the basis of a position and an attitude of the imaging unit 20 that correspond to a detection result of a position and an attitude of each section of a support section (e.g. an arm) supporting the imaging unit 20, for example. Note that the details of an example of a correction method of a parallax difference between viewpoint images will be separately described later.

In addition, as another example, the image processing section 101a may correct a magnification difference between viewpoint images on the basis of the magnification difference correction data. In addition, the image processing section 101a may correct a difference in color properties between parallax images on the basis of the color correction data. In addition, the image processing section 101a may correct a difference in white balance between parallax images on the basis of the white balance correction data. In addition, the image processing section 101a may correct a white spot generated by a pixel defect in the imager of the imaging section 201a, on the basis of the white spot correction data. Note that the image processing sections 101a and 101b correspond to an example of a "correction section".

In the above-described manner, the image processing section 101a performs the above-described various types of image processing and correction processing on the viewpoint image acquired from the imaging section 201a, and outputs the processed viewpoint image to the 3D image generation section 105 positioned on a subsequent stage.

The 3D image generation section 105 acquires, from the image processing sections 101a and 101b, viewpoint images that have been respectively captured by the imaging sections 201a and 201b, and been subjected to the various types of image processing and correction processing. Then, the 3D image generation section 105 generates a parallax image having a set parallax for causing the user to observe a 3D image, on the basis of the acquired viewpoint images (i.e. the left-eye image and the right-eye image), and causes the parallax image to be displayed on the display device 40. Note that the display device 40 corresponds to the display device 550 described with reference to FIG. 1.

Herein, as an example of more detailed, processing of the 3D image generation section 105, the description will be given of processing performed in a case in which the user is caused to observe a 3D image on the basis of the glasses-free 3D picture technology. In this case, for example, the 3D image generation section 105 calculates, on the basis of an interval between assumed viewpoints of the user (i.e. an interval between the left eye and the right eye), a parallax value to be set to an image to be observed at each viewpoint. Then, the 3D image generation section 105 generates a so-called multiple view image in which viewpoint images to be respectively observed by the left eye and the right eye of the user are presented on the basis of the calculation result of the parallax value, and causes the generated multiple view image to be displayed on the display device 40. The viewpoint images (i.e. the right-eye image and the left-eye image) presented in the multiple view image are separated by an optical member such as a lenticular plate and a parallax barrier that is provided in the display device 40, for example, and respectively observed at corresponding viewpoints of the user (i.e. the right eye and the left eye). It thereby becomes possible for the user to observe a 3D image via the display device 40.

Note that the above-described processing for causing a 3D image to be observed is merely an example, and needless to say, may be appropriately changed in accordance with a method and a configuration for causing a 3D image to be observed.

An example of a functional configuration of the medical stereoscopic observation device according to the present embodiment has been described above with reference to FIGS. 5 to 7. Note that the above description has been given of an example in which correction data corresponding to the properties of the imaging sections 201a and 201b of the imaging unit 20 are stored in the correction data storage section 205 of the imaging unit 20, and the correction data are transferred to the image processing device 10 and the imaging control device 30. On the other hand, if the image processing device 10 and the imaging control device 30 can acquire (refer to) correction data corresponding to the connected imaging unit 20, a transfer source of the correction data and a location where the correction data is held are not specifically limited. As a specific example, correction data, may be stored in an external server or the like. In this case, the image processing device 10 and the imaging control device 30 are only required to acquire, from the server, correction data corresponding to the imaging unit 20, in accordance with the imaging unit 20 connected to the medical stereoscopic observation device 1.

In addition, a functional configuration of the medical stereoscopic observation device according to the present embodiment that has been described above with reference to FIG. 5 is merely an example, and the functional configuration is not necessarily limited only to the example described above. For example, as described above, the imaging unit 20 may also be configured to be attachable and removable, and the imaging unit 20 having different properties of the optical system 203 and the imaging sections 201a and 201b (e.g. imager, etc.) may be connected in accordance with purposes. In addition, a portion of the imaging unit 20 that corresponds to the optical system 203 may be configured to be attachable and removable as an optical system unit (lens group). In this case, among the above-described correction data, data corresponding to the property of the optical system 203 may be stored in a storage region of the optical system unit.

In addition, at least a part of the above-described medical stereoscopic observation device may be integrally configured. For example, the configurations of the image processing device 10 and the configurations of the imaging control device 30 may be mounted on one basement or one chip. In addition, a part of the configurations of the above-described medical stereoscopic observation device may be provided on the outside (e.g. server, etc.) of the medical stereoscopic observation device. As a specific example, processing corresponding to the 3D image generation section 105 of the image processing device 10 may be executed by an external device such as a server.

<<4. Processes>>

Subsequently an example of a flow of a series of processes of the medical stereoscopic observation device according to the present embodiment will be described with focusing attention especially on processing related to correction of a parallax difference between viewpoint images that is performed by the image processing device 10, and processing related to correction of a lens position that is performed by the imaging control device 30.

<4.1. Processing Related to Correction of Parallax Difference>

Figure 8:
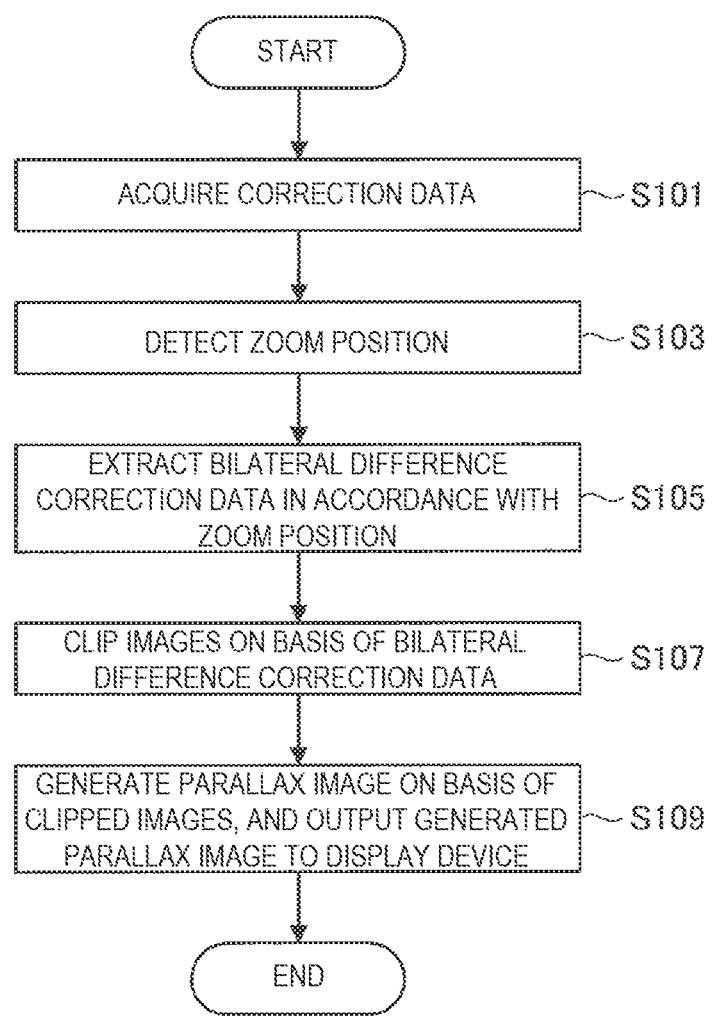
FIG. 8 is a flow chart illustrating an example of a flow of a series of processes of a medical stereoscopic observation device according to the embodiment.

First of all, with reference to FIG. 8, the description will be given of an example of a flow of a series of processes performed in a case in which the image processing device 10 performs, on viewpoint images (i.e. the left-eye image and the right-eye image) captured by the imaging unit 20, correction of a parallax difference between the viewpoint images, on the basis of correction data transferred from the imaging unit 20. FIG. 8 is a flow chart illustrating an example of a flow of a series of processes of the medical stereoscopic observation device according to the present embodiment, and illustrates a flow of processing related to the correction of a parallax difference that is performed by the image processing device 10.

First of all, the image processing device 10 acquires, from the imaging unit 20 connected to the medical stereoscopic observation device 1, correction data corresponding to the imaging unit 20, and holds the correction data in a predetermined storage region (the storage section 103) as cache (S101).

After that, the image processing device 10 detects a zoom position of the imaging unit 20. In this case, by acquiring information indicating a detection result of a zoom position, from the imaging unit 20, for example, the image processing device 10 may recognize the zoom position. In addition, as another example, by acquiring information corresponding to a control result of a zoom position, from the imaging control device 30 that controls an operation of the imaging unit 20, the image processing device 10 may recognize the zoom position (S103). Then, in accordance with a detection result of a zoom position, the image processing device 10 extracts bilateral difference correction data corresponding to the zoom position, from the correction data held as cache (S105).

After that, the image processing device 10 performs, on viewpoint images (i.e. the left-eye image and the right-eye image) captured by the imaging unit 20, processing related to correction of a parallax difference between the viewpoint images, on the basis of the extracted bilateral difference correction data.

Figure 9:
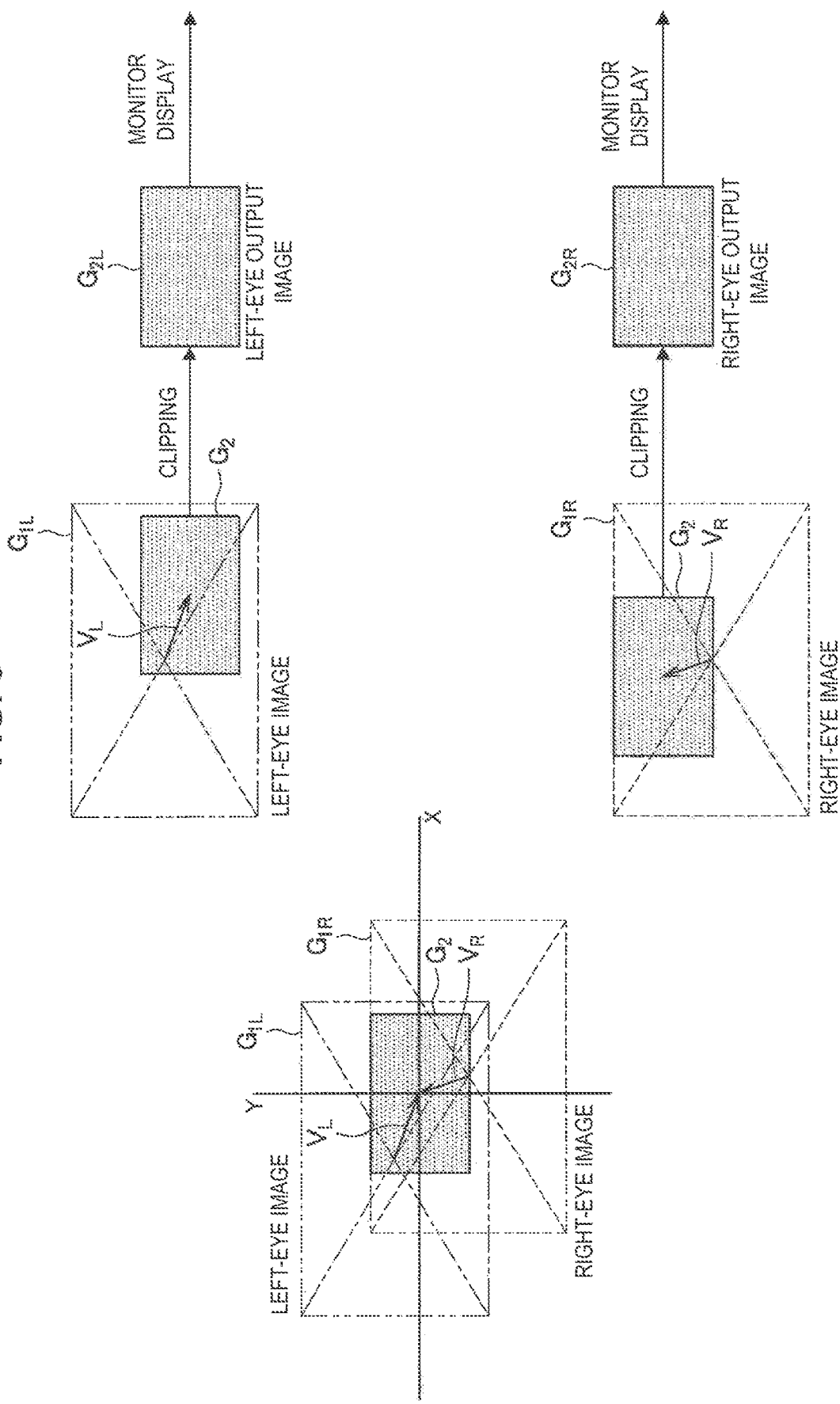
FIG. 9 is an explanatory diagram for explaining an example of processing related to correction of a parallax difference.

Herein, an example of processing related to the correction of a parallax difference that is performed by the image processing device 10 will be described with reference to FIG. 9. FIG. 9 is an explanatory diagram for explaining an example of processing related to correction of a parallax difference.

For example, a diagram on the left side of FIG. 9 diagrammatically illustrates a positional relationship between a range to be imaged as a left-eye image, and a range to be imaged as a right-eye image, in a case in which a parallax difference is generated. Note that the X direction corresponds to a horizontal direction of each viewpoint image. In addition, the Y direction corresponds to a vertical direction of each viewpoint image. In addition, a reference numeral $G_{1L}$ denotes a range to be imaged as a left-eye image. In addition, a reference numeral $G_{1R}$ denotes a range to be imaged as a right-eye image.

First of all, the image processing device 10 identifies a reference position for correcting a parallax difference of viewpoint images. As a specific example, as illustrated in FIG. 3, the image processing device 10 may identify, as a reference position, the focal position $O_{11}$ of the imaging unit 20 (i.e. a position serving as a reference of the rotation of the imaging unit 20 at the time of pivot observation). Note that, for the sake of convenience, this description will be given assuming that, in the diagram on the left side of FIG. 9, an intersection point of the X-axis and the Y-axis is a reference position.

After that, the image processing device 10 calculates a shift $V_L$ between the reference position and a center position of a left-eye image (i.e. a center position of the imaging range $G_{1L}$), on the basis of information indicating a shift of the center position of the left-eye image, among the extracted bilateral difference correction data. In a similar manner, the image processing device 10 calculates a shift $V_R$ between the reference position and a center position of a right-eye image (i.e. a center position of the imaging range $G_{1R}$), on the basis of information indicating a shift of the center position of the right-eye image, among the extracted bilateral difference correction data. In addition, the image processing device 10 calculates an overlap region between the imaging range $G_{1L}$ of the left-eye image and the imaging range $G_{1R}$ of the right-eye image, on the basis of the calculated shifts $V_L$ and $V_R$ of the center positions with respect to the reference position. Then, the image processing device 10 identifies a range $G^2$ to be clipped as an output image, from the overlap region between the imaging range $G_{1L}$ of the left-eye image and the imaging range $G_{1R}$ of the right-eye image, using the reference position as a center.

Then, the image processing device 10 clips a partial image corresponding to the range $G_2$, from each of the left-eye image and the right-eye image, on the basis of an identification result of the range $G_2$. For example, a diagram shown on the upper right of FIG. 9 illustrates an overview of processing of clipping a partial image from a left-eye image. More specifically, the image processing device 10 clips, as a partial image, an image of a region corresponding to the range $G_2$, in the imaging range $G_{1L}$ of a left-eye image, from the left-eye image. At this time, the center of the partial image to be clipped from the left-eye image substantially matches the reference position. Note that in the following description, the clipped partial image will also be referred to as a "left-eye output image $G_{2L}$".

In a similar manner, a diagram shown on the lower right of FIG. 9 illustrates an overview of processing of clipping a partial image from a right-eye image. More specifically, the image processing device 10 clips, as a partial image, an image of a region corresponding to the range $G_2$, in the imaging range $G_{1R}$ of a right-eye image, from the right-eye image. At this time, the center of the partial image to be clipped from the right-eye image substantially matches the reference position. Note that in the following description, the clipped partial image will also be referred to as a "right-eye output image $G_{2R}$".

Then, as illustrated in FIG. 8, the image processing device 10 generates a parallax image having a set parallax for causing the user to observe a 3D image, on the basis of the clipped left-eye output image $G_{2L}$, and right-eye output image $G_{2R}$, and causes the parallax image to be displayed on the display device 40 (S109).

An example of a flow of a series of processes performed in a case in which the image processing device 10 performs, on viewpoint images captured by the imaging unit 20, correction of a parallax difference between the viewpoint images, on the basis of correction data transferred from the imaging unit 20 has been described above with reference to FIG. 8. By the processing as described above, a parallax difference is corrected, and the center positions of images to be respectively observed by the left eye and the right eye of the user match. Thus, it becomes possible for the user to observe a sharper stereoscopic 3D image of an observation target that has suppressed generation of deformation.

In addition, as described above, by correcting a parallax difference using the focal position $O_{11}$ of the imaging unit 20 as a reference position, it becomes possible to suppress the generation of a parallax difference between viewpoint images even if the imaging unit 20 is rotated with respect to an observation target as illustrated in FIG. 3, for example. In other words, it becomes possible for the user to observe a sharper 3D image having suppressed generation of deformation, even in the case of observing images obtained by imaging an affected area serving as an observation target, from mutually different directions.

<4.2. Processing Related to Correction of Lens Position>

Figure 10:
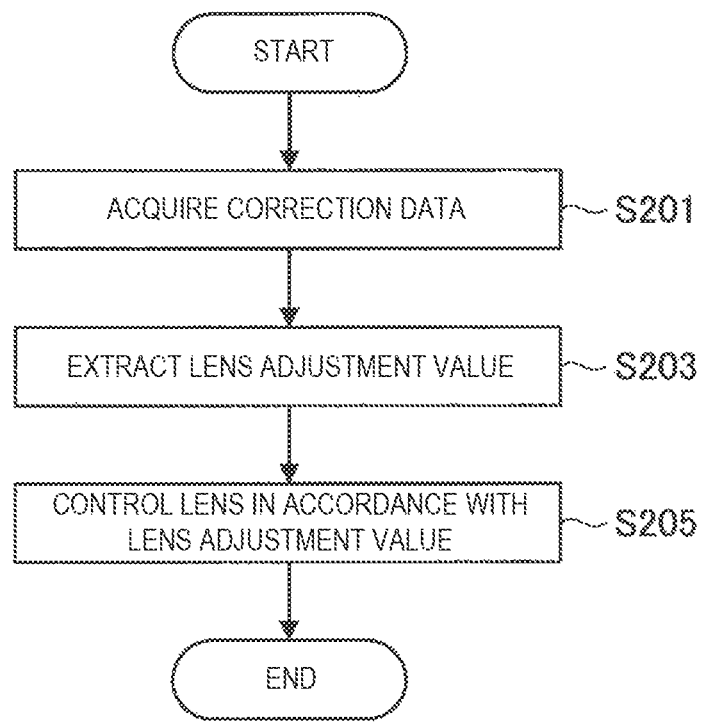
FIG. 10 is a flow chart illustrating another example of a flow of a series of processes of a medical stereoscopic observation device according to the embodiment.

Subsequently, with reference to FIG. 10, the description will be given of an example of a flow of processing performed in a case in which the imaging control device 30 controls an operation related to the capturing of images that is performed by the imaging unit 20, on the basis of correction data transferred from the imaging unit 20, with focusing attention especially on the case of correcting a lens position (default position of a lens). FIG. 10 is flow chart illustrating another example of a flow of a series of processes of the medical stereoscopic observation device according to the present embodiment, and illustrates a flow of processing related to the correction of a lens position that is performed by the imaging control device 30.

First of all, the imaging control device 30 acquires, from the imaging unit 20 connected to the medical stereoscopic observation device 1, correction data corresponding to the imaging unit 20, and holds the correction data in a predetermined storage region (the storage section 303) as cache (S201).

After that, the imaging control device 30 extracts lens position correction data (i.e. lens position correction data corresponding to a variation in the assembly of the optical system 203 of the connected imaging unit 20) from the correction data held as cache (S203).

Then, on the basis of the extracted lens position correction data, the imaging control device 30 corrects a shift in lens positions (e.g. default positions of lenses) between lenses for forming images of an imaging target on the respective imaging sections 201a and 201b, among various lenses constituting the optical system 203 of the imaging unit 20 (S205).

With reference to FIG. 10, the description has been given above of an example of a flow of processing performed in a case in which the imaging control device 30 controls an operation related to the capturing of images that is performed by the imaging unit 20, on the basis of correction data transferred from the imaging unit 20, with focusing attention especially on the case of correcting a lens position. By the processing as described above, it becomes possible to correct a shift in lens positions between optical systems for respectively capturing a left-eye image and a right-eye image. For this reason, because it becomes possible to suppress the generation of deformation of a 3D image that is caused by the shift in lens positions, it becomes possible for the user to observe a sharper stereoscopic image of an observation target.

<<5. Hardware Configuration>>

Figure 11:
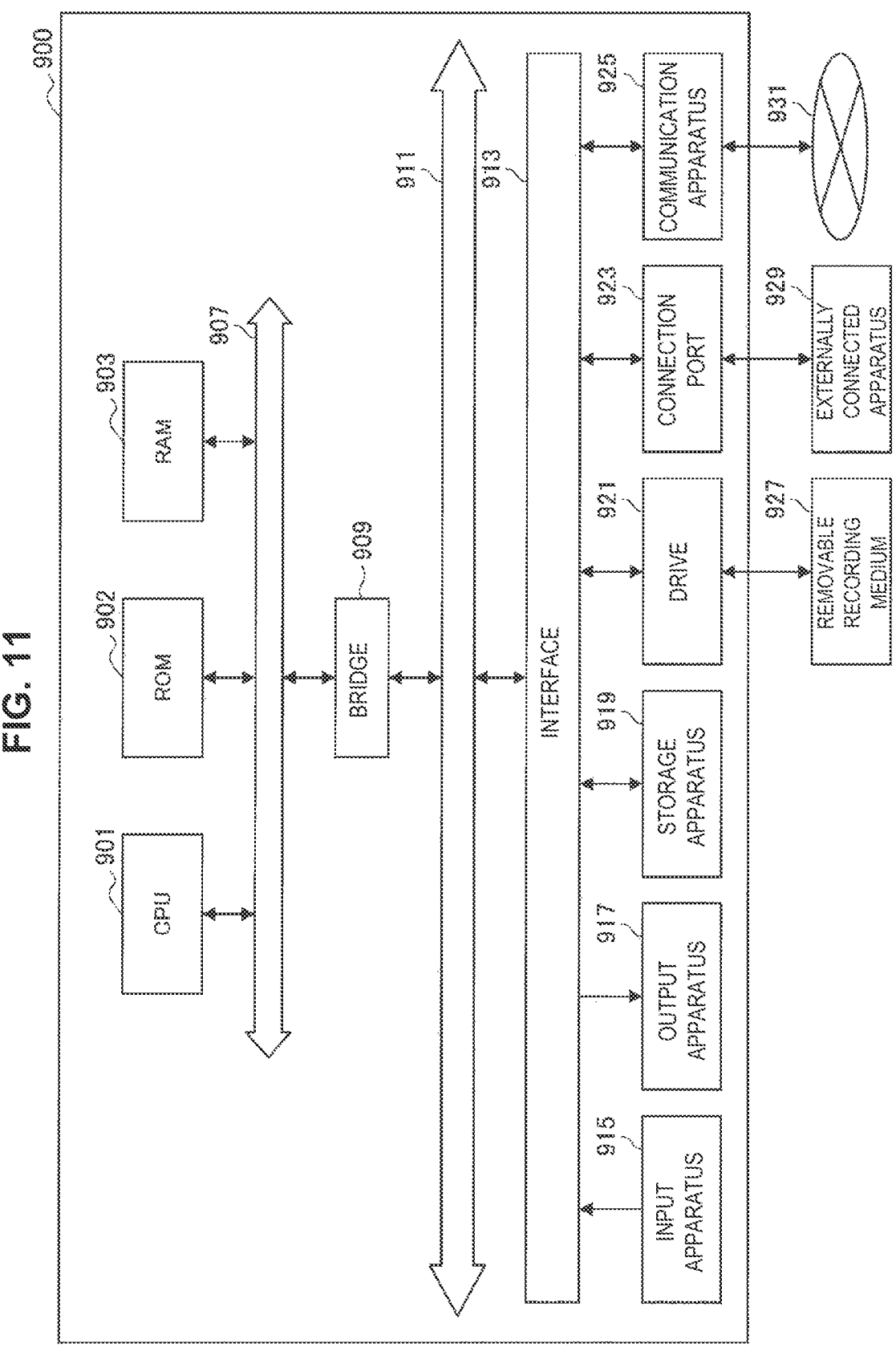
FIG. 11 is a function block diagram illustrating an example configuration of the hardware configuration of an information processing device constituting a medical stereoscopic observation system according to the embodiment.

Next, a hardware configuration of an information processing apparatus 900 constituting a medical stereoscopic observation device according to the present embodiment, such as the surgical video microscope device or the image processing device described earlier, will be described in detail with reference to FIG. 11. FIG. 11 is a function block diagram illustrating an example configuration of the hardware configuration of an information processing apparatus 900 constituting a medical stereoscopic observation system according to an embodiment of the present disclosure.

The information processing apparatus 900 constituting a medical stereoscopic observation system according to the present embodiment is equipped primarily with a CPU 901, ROM 903, and RAM 905. Additionally, the information processing apparatus 900 may also be equipped with a host bus 907, a bridge 909, an external bus 911, an interface 913, an input apparatus 915, an output apparatus 917, a storage apparatus 919, a drive 921, a connection port 923, and a communication apparatus 925.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like. Note that the image processing sections 101a and 101, and the 3D image generation section 105 described earlier with reference to FIG. 5 may be realized by the CPU 901, for example.

The host bus 907 is connected to the external bus 911 such as a PCI (Peripheral Component Interconnect/Interface) bus via the bridge 909. Additionally, the input apparatus 915, the output apparatus 917, the storage apparatus 919, the drive 921, the connection port 923, and the communication apparatus 925 are connected to the external bus 911 via the interface 913.

The input apparatus 915 is an operation mechanism operated by a user, such as a mouse, a keyboard, a touch panel, buttons, a switch, a lever, or a pedal. Also, the input apparatus 915 may be a remote control mechanism (a so-called remote control) using, for example, infrared light or other radio waves, or may be an externally connected apparatus 929 such as a mobile phone or a PDA conforming to the operation of the information processing apparatus 900. Furthermore, the input apparatus 915 generates an input signal based on, for example, information which is input by a user with the above operation mechanism, and is configured from an input control circuit for outputting the input signal to the CPU 901. The user of the information processing apparatus 900 can input various data to the information processing apparatus 900 and can instruct the information processing apparatus 900 to perform processing by operating this input apparatus 915.

The output apparatus 917 is configured from a device capable of visually or audibly notifying acquired information to a user. Examples of such device include display apparatuses such as a CRT display apparatus, a liquid crystal display apparatus, a plasma display apparatus, an EL display apparatus and lamps, audio output apparatuses such as a speaker and a headphone, a printer, and the like. For example, the output apparatus 917 outputs a result obtained by various processing performed by the information processing apparatus 900. More specifically, the display apparatus displays, in the form of texts or images, a result obtained by various processes performed by the information processing apparatus 900. On the other hand, the audio output apparatus converts an audio signal such as reproduced audio data and sound data into an analog signal, and outputs the analog signal. Note that the display device 40 described earlier with reference to FIG. 5 may be realized by the output apparatus 917, for example.

The storage apparatus 919 is a device for storing data configured as an example of a storage unit of the information processing apparatus 900 and is used to store data. The storage apparatus 919 is configured from, for example, a magnetic storage apparatus such as a HDD (Hard Disk Drive), a semiconductor storage apparatus, an optical storage apparatus, or a magneto-optical storage apparatus. This storage apparatus 919 stores programs to be executed by the CPU 901, and various data. Note that the storage section 103 described earlier with reference to FIG. 5 may be realized by the storage apparatus 919, for example.

The drive 921 is a reader/writer for recording medium, and is embedded in the information processing apparatus 900 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (a registered trademark) medium. The removable recording medium 927 may be a CompactFlash (CF; a registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing apparatuses to directly connect to the information processing apparatus 900. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (a registered trademark) (High-Definition Multimedia Interface) port, and the like. By the externally connected apparatus 929 connecting to this connection port 923, the information processing apparatus 900 directly obtains various data from the externally connected apparatus 929 and provides various data to the externally connected apparatus 929.

The communication apparatus 925 is a communication interface configured from, for example, a communication apparatus for connecting to a communication network 931. The communication apparatus 925 is, for example, a wired or wireless LAN (Local Area Network), Bluetooth (registered trademark), a communication card for WUSB (Wireless USB), or the like. Alternatively, the communication apparatus 925 may be a router for optical communication, a router for ADSL (Asymmetric Digital Subscriber Line), a modem for various communications, or the like. This communication apparatus 925 can transmit and receive signals and the like in accordance with a predetermined protocol such as TCP/IP on the Internet and with other communication apparatuses, for example.

The communication network 931 connected to the communication apparatus 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the information processing apparatus 900 constituting a medical stereoscopic observation system according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment. Note that, although not illustrated in FIG. 11, the various structural elements corresponding to the information processing apparatus 900 constituting a medical stereoscopic observation system (in other words, a surgical video microscope device or an image processing device) obviously are provided.

Note that it is also possible to develop a computer program for realizing the respective functions of the information processing apparatus 900 constituting a medical stereoscopic observation system according to the present embodiment as described above, and implement the computer program in a personal computer or the like. In addition, a computer-readable recording medium storing such a computer program may also be provided. The recording medium may be a magnetic disc, an optical disc, a magneto-optical disc, or flash memory, for example. Furthermore, the above computer program may also be delivered via a network, for example, without using a recording medium.

<<6. Conclusion>>

As described above, in the medical stereoscopic observation device according to the present embodiment, the imaging unit 20 includes the imaging section 201a for capturing a left-eye image, and the imaging section 201b for capturing a right-eye image. In addition, the imaging unit 20 is rotatably held by a support section (e.g. an arm section 405 illustrated in FIG. 2). For example, the imaging unit 20 may be held by the support section so as to be rotatable with respect to a subject (e.g. an affected area serving as an observation target). In addition, correction data for correcting various differences caused by an error related to the capturing of images between the imaging sections 201a and 201b are stored in the correction data storage section 205 of the imaging unit 20. The correction data are transferred from the imaging unit 20 to the image processing device 10, and held in the storage section 103 of the image processing device 10 as cache. Then, the image processing device 10 corrects a shift (e.g. parallax difference) between a left-eye image and a right-eye image on the basis of the correction data, using, for example, a position serving as a reference of the rotation of the imaging unit 20 (e.g. the focal position $O_{11}$ of the imaging unit 20 illustrated in FIG. 3), as a reference position.

By the configuration as described above, it becomes possible for the user to observe a sharper stereoscopic 3D image of an observation target that has suppressed generation of deformation. In addition, according to the medical stereoscopic observation device according to the present embodiment, it becomes possible for the image processing device 10 to correct a shift between parallax images that is caused by an error between the imaging sections 201a and 201b, by correction data acquired from the imaging unit 20. Thus, for example, it becomes unnecessary for the image processing device 10 to execute, in real time, the detection of a shift between viewpoint images, and various types of analysis processing for correcting the shift, and load of image processing performed on each viewpoint image is reduced. It eventually becomes possible to reduce power consumption.

In addition, as described above, by correcting a parallax difference using the focal position $O_{11}$ of the imaging unit 20 as a reference position, it becomes possible to suppress the generation of a parallax difference between viewpoint images even if the imaging unit 20 is rotated with respect to an observation target as illustrated in FIG. 3, for example. In other words, it becomes possible for the user to observe a sharper 3D image having suppressed generation of deformation, even in the case of observing images obtained by imaging an affected area serving as an observation target, from mutually different directions.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not imitative. That is, with or in the place of the above effects, the technology according to the present disclosure may achieve other effects that are clear to those skilled in the art from the description of this specification.

Additionally, the present technology may also be configured as below.

(1)

A medical stereoscopic observation device including:

an acquisition section configured to acquire, from an imaging unit including a first imaging section configured to capture a left-eye image and a second imaging section configured to capture a right-eye image, correction data for correcting an error related to capturing of an image between the first imaging section and the second imaging section, the imaging unit being rotatably held by a support section; and a correction section configured to correct a difference of parallax between the left-eye image and the right-eye image on a basis of the correction data, using a position corresponding to a rotation axis of the imaging unit as a reference position.

(2)

The medical stereoscopic observation device according to (1), in which the correction section corrects the difference of parallax by clipping, respectively from the left-eye image and the right-eye image, partial images having image centers substantially matching the position corresponding to the rotation axis, as a new left-eye image and a new right-eye image.

(3)

The medical stereoscopic observation device according to (1) or (2), in which the correction section corrects the difference of parallax by clipping, respectively from the left-eye image and the right-eye image, partial images of a region in which respective imaging ranges of the first imaging section and the second imaging section overlap, as a new left-eye image and a new right-eye image.

(4)

The medical stereoscopic observation device according to any one of (1) to (3), in which the correction data includes data for correcting the error between the first imaging section and the second imaging section, for each magnification percentage of zoom, and the correction section corrects the difference of parallax on a basis of the data corresponding to the magnification percentage of the zoom that is set for the first imaging section and the second imaging section.

(5)

The medical stereoscopic observation device according to any one of (1) to (4), in which the correction section corrects a difference in magnification percentage of zoom between the left-eye image and the right-eye image, on a basis of the correction data.

(6)

The medical stereoscopic observation device according to any one of (1) to (5), in which the correction section corrects a difference in color property between the left-eye image and the right-eye image, on a basis of the correction data.

(7)

The medical stereoscopic observation device according to any one of (1) to (6), in which the imaging unit is supported by the support section such that the imaging unit becomes rotatable with respect to a subject, and the reference position is a focal position of the imaging unit.

(8)

The medical stereoscopic observation device according to any one of (1) to (7), including the support section.

(9)

The medical stereoscopic observation device according to (8), in which the support section is configured to be attachable to and removable from the imaging unit, and the correction section corrects the difference of parallax on a basis of the correction data acquired from the imaging unit attached to the support section.

(10)

The medical stereoscopic observation device according to (8), including the imaging unit.

(11)

The medical stereoscopic observation device according to any one of (8) to (10), in which the support section includes a control, section configured to control an operation of the imaging unit on a basis of the correction data acquired from the imaging unit.

(12)

The medical stereoscopic observation device according to (11), in which the control section corrects a shift in positions of optical systems between the first imaging section and the second imaging section, on a basis of the correction data.

(13)

A medical stereoscopic observation method including:

acquiring, from an imaging unit including a first imaging section configured to capture a left-eye image and a second imaging section configured to capture a right-eye image, correction data for correcting an error related to capturing of an image between the first imaging section and the second imaging section, the imaging unit being rotatably held by a support section; and correcting, by a processor, a difference of parallax between the left-eye image and the right-eye image on a basis of the correction data, using a position corresponding to a rotation axis of the imaging unit as a reference position.

(14)

A program for causing a computer to execute:

acquiring, from an imaging unit including a first imaging section configured to capture a left-eye image and a second imaging section configured to capture a right-eye image, correction data for correcting an error related to capturing of an image between the first imaging section and the second imaging section, the imaging unit'being rotatably held by a support section; and correcting a difference of parallax between the left-eye image and the right-eye image on a basis of the correction data, using a position corresponding to a rotation axis of the imaging unit as a reference position.

REFERENCE SIGNS LIST 1 medical stereoscopic observation device
10 image processing device
101a, 101b image processing section
103 storage section
105 3D image generation section
20 imaging unit
201a, 201b imaging section
203 optical system
205 correction data storage section
207 drive section
30 imaging control device
301 control section 303 storage section
40 display device

The invention claimed is:
1. A medical stereoscopic observation device comprising:
circuitry configured to
acquire, from an imaging device including a first imaging sensor configured to capture a left-eye image and a second imaging sensor configured to capture a right-eye image, correction data for correcting an error related to capturing of an image between the first imaging sensor and the second imaging sensor, the imaging device being rotatably held by a support section, wherein the correction data includes data for correcting the error between the first imaging sensor and the second imaging sensor, for each magnification of zoom,
store the correction data,
correct a difference of parallax based on the data corresponding to the magnification of the zoom that is set for the first imaging sensor and the second imaging sensor, and
correct the difference of parallax between the left-eye image and the right-eye image based on the correction data, wherein the circuitry for correcting the difference of parallax between the left eye image and the right-eye image based on the correction data is further configured to
identify a reference position, the reference position corresponding to a rotation axis of the imaging device and being a focal position of the imaging device,
wherein the difference of parallax is corrected by clipping, respectively from the left-eye image and the right-eye image, partial images having image centers substantially matching the reference position corresponding to the rotation axis, as a new left-eye image and a new right-eye image.
2. The medical stereoscopic observation device according to claim 1, wherein the circuitry is further configured to:
correct the difference of parallax by clipping, respectively from the left-eye image and the right-eye image, partial images of a region in which respective imaging ranges of the first imaging sensor and the second imaging sensor overlap, as a new left-eye image and a new right-eye image.
3. The medical stereoscopic observation device according to claim 1, wherein the circuitry is further configured to:
correct a difference in magnification of zoom between the left-eye image and the right-eye image based on the correction data.
4. The medical stereoscopic observation device according to claim 1, wherein circuitry is further configured to:
correct a difference in color property between the left-eye image and the right-eye image based on the correction data.
5. The medical stereoscopic observation device according to claim 1, wherein the imaging device is supported by the support section such that the imaging device becomes rotatable with respect to a subject.
6. The medical stereoscopic observation device according to claim 1, further comprising:
the support section.
7. The medical stereoscopic observation device according to claim 6, wherein the support section is configured to be attachable to and removable from the imaging device, and the circuitry is further configured to correct the difference of parallax based on the correction data acquired from the imaging device.
8. The medical stereoscopic observation device according to claim 6, further comprising:
the imaging device.
9. The medical stereoscopic observation device according to claim 6, wherein the support section includes a controller configured to control an operation of the imaging device based on the correction data acquired from the imaging device.
10. The medical stereoscopic observation device according to claim 9, wherein the controller corrects a shift in positions of optical systems between the first imaging sensor and the second imaging sensor based on the correction data.
11. A medical stereoscopic observation method comprising:
acquiring, from an imaging device including a first imaging sensor configured to capture a left-eye image and a second imaging sensor configured to capture a right-eye image, correction data for correcting an error related to capturing of an image between the first imaging sensor and the second imaging sensor, the imaging device being rotatably held by a support section, wherein the correction data includes data for correcting the error between the first imaging sensor and the second imaging sensor, for each magnification of zoom;
storing the correction data;
correcting a difference of parallax based on the data corresponding to the magnification of the zoom that is set for the first imaging sensor and the second imaging sensor; and
correcting, by a processor, a difference of parallax between the left-eye image and the right-eye image based on the correction data, wherein correcting the difference of parallax between the left eye image and the right-eye image based on the correction data includes
identifying a reference position, the reference position corresponding to a rotation axis of the imaging device and being a focal position of the imaging device,
wherein the difference of parallax is corrected by clipping, respectively from the left-eye image and the right-eye image, partial images having image centers substantially matching the reference position corresponding to the rotation axis, as a new left-eye image and a new right-eye image.
12. A non-transitory computer-readable storage medium storing computer-readable instructions thereon which, when executed by a computer, cause the computer to perform a method, the method comprising:
acquiring, from an imaging device including a first imaging sensor configured to capture a left-eye image and a second imaging sensor configured to capture a right-eye image, correction data for correcting an error related to capturing of an image between the first imaging sensor and the second imaging sensor, the imaging device being rotatably held by a support section, wherein the correction data includes data for correcting the error between the first imaging sensor and the second imaging sensor, for each magnification of zoom;

storing the correction data;
correcting a difference of parallax based on the data corresponding to the magnification of the zoom that is set for the first imaging sensor and the second imaging sensor; and
correcting a difference of parallax between the left-eye image and the right-eye image based on the correction data, wherein correcting the difference of parallax between the left eye image and the right-eye image based on the correction data includes
identifying a reference position, the reference position corresponding to a rotation axis of the imaging device and being a focal position of the imaging device,
wherein the difference of parallax is corrected by clipping, respectively from the left-eye image and the right-eye image, partial images having image centers substantially matching the reference position corresponding to the rotation axis, as a new left-eye image and a new right-eye image.

* * * * *